United States Patent [19]
Brake

[11] Patent Number: 5,264,614
[45] Date of Patent: Nov. 23, 1993

[54] RECOVERY OF POLYHYDROXY ACIDS

[75] Inventor: Loren D. Brake, Wilmington, Del.

[73] Assignee: E. I. Du Pont de Nemours and Company, Wilmington, Del.

[21] Appl. No.: 796,274

[22] Filed: Nov. 22, 1991

[51] Int. Cl.$^5$ ............... C07C 69/66; C07C 59/08; C07C 51/42
[52] U.S. Cl. ................. 560/179; 562/580; 562/589; 549/274; 525/450; 528/495; 528/496
[58] Field of Search ............ 528/300; 560/179; 562/580; 549/274

[56] References Cited

U.S. PATENT DOCUMENTS

| | | | |
|---|---|---|---|
| 2,231,953 | 2/1941 | Ruxicka | 92/17 |
| 3,284,417 | 11/1966 | Hostettler et al. | 260/78.3 |
| 3,578,700 | 5/1971 | Klootwijk et al. | 260/484 |
| 4,727,163 | 2/1988 | Bellis | 549/274 |
| 4,797,468 | 1/1989 | De Vries | 528/354 |
| 4,835,293 | 5/1989 | Bhatia | 549/274 |

FOREIGN PATENT DOCUMENTS

90/01521 2/1990 PCT Int'l Appl.

Primary Examiner—José G. Dees
Assistant Examiner—Porfirio Nazario

[57] ABSTRACT

Polyhydroxyacid (PHA) is recovered by heating under pressure in the presence of a $C_1$–$C_6$ alcohol, and optionally also water.

19 Claims, No Drawings

RECOVERY OF POLYHYDROXY ACIDS

BACKGROUND OF THE INVENTION

1. Field of the Invention

The present invention relates to the recovery of polyhydroxy acid (PHA) by heating under pressure in the presence of a $C_1$ to $C_6$ alcohol, and optionally also water. More specifically, the present invention relates to the recovery of hydroxy acid value from a polyhydroxy acid polymer-containing source such as food container trash.

2. Description of the Related Art

Shaped articles of high molecular weight (at least 10,000, and normally 15,000 to 500,000 MW) polyhydroxy acids (PHA), particularly polylactic acid (PLA, polylactide), polyglycolic acid (PGA, polyglycolide), and copolymers thereof, have been known for years. An important property of these polymers is that they are slowly hydrolyzable and thereafter biodegradable to environmentally benign by-products. Consequently high molecular weight PHA polymer shaped articles are finding increasing application as replacements for polystyrene and other non-degradable polymers in products that will degrade in a landfill, such as fast food containers (Sinclair et al., WO90/01521, 22 Feb. 1990).

While this is a significant step in minimizing litter and long-term landfill disposal, discarding high molecular weight polyhydroxy acid articles for natural destruction by hydrolysis has the cost penalty of discarding the valuable polyhydroxy acid.

Although the hydrolysis of PHAs is well known, heretofore it has not been achievable in a time frame to permit recovery from other insoluble waste and reuse of the valuable hydroxy acid (HA) moities. In fact, although degradable, the time for degradation of high molecular weight PHAs is so long as not to offer a significant lessening burden on landfills.

Thus, there is a need for an economical method to recover and recycle the polyhydroxy acid content of this source of insoluble waste material and avoid burdening landfills with this waste.

The most economical routes for PHA production start with the acid such as lactic acid. The acid is converted to an ester, dimerized to a cyclic ring such as lactide, which is then polymerized to PHA. This is a complicated and costly process. See Bhatia U.S. Pat. No. 4,835,293 (May 30, 1989); Bellis U.S. Pat. No. 4,727,163 (Feb. 23, 1988); Klootwijk U.S. Pat. No. 3,578,700; Hostettler et. al. U.S. Pat. No. 3,284,417; and De Vries U.S. Pat. No. 4,797,468 (Jan. 10, 1989).

Bhatia, U.S. Pat. No. 5,136,057, discloses the depolymerization of low molecular weight oligomers remaining after PHA polymerization. This patent application does not address the problem of recovery of the monomeric values from used high molecular weight PHA articles.

Copending and commonly assigned U.S. patent application Ser. Nos. 07/797,502, 07/797,503, 07/796,273 and 07/796,272 disclose the recovery of PHAs, respectively, in the presence of an alcohol and an acid catalyst; in the presence of water and acid; in water under heat and pressure; and in the presence of specific amines.

The aforementioned patent applications are incorporated herein by reference.

SUMMARY OF THE INVENTION

The present invention provides a method of recovering polyhydroxyacid polymer comprising:

(a) mixing the polymer with $C_1$-$C_6$ alkyl alcohol present in an amount of at least 1 mole of alcohol per acid equivalent; and (b) heating the mixture to solubilize the PHA.

In one embodiment of the invention the polymer is selected from group consisting of polylactide, polyglycolide, and polymers containing a major proportion of polylactide or polyglycolide copolymerized with up to 30% of another monomer selected from the group consisting of psilon-caprolactone, delta-valerolactone, 1,5-dioxepen-2-one, 1,4-dioxan-2-one, beta-butyrolactone, beta-propiolactone, 6-methyl-2,5-morpholinedione and mixtures thereof. Typically the temperature of the process is in the range 100° to 200° C. and the time is in the range of ¼ to 16 hours.

The present invention further provides a method of recovering polyhydroxy acid value from a polyhydroxy acid polymer-containing source comprising the steps of:

(a) contacting a polyhydroxy acid polymer-containing material, wherein said polyhydroxy acid polymer-containing material is contaminated with or constitutes trash, with at least one mole of a $C_1$ to $C_6$ alkyl alcohol per mole of hydroxy acid equivalent of said polyhydroxy acid polymer while maintaining the resulting mixture at sufficient temperature and pressure for a sufficient time to solubilize said polymer and form a liquid phase of enhanced polyhydroxy acid value; and (b) thereafter isolating and recovering said liquid phase.

DESCRIPTION OF THE PREFERRED EMBODIMENTS

The present invention is a process for economically rapid recovery of the valuable PHA content of high molecular weight PHAs, thereby eliminating landfill and biodegradation of the PHA products, particularly fast food containers such as plates, cups, and solid food containers.

Specifically, the present invention relates to the recovery of high molecular weight PHAs of at least 10,000 and normally 15,000 to 500,000 MW by dissolving the PHA content in a $C_1$ to $C_6$ alcohol at elevated temperature to render the PHA soluble in the alcohol; and crystallizing the dissolved PHA by cooling the alcohol/PHA solution. The PHA can then be recovered from the liquid medium by known mechanical means such as decanting, filtering or centrifuging; or the alcohol/PHA can be used directly, or with some concentration, in the preparation of high molecular weight PHA.

In some cases, it may be desirable to add some water to the alcohol starting liquid to partially depolymerize the PHA to facilitate the recovery and separation of the PHA depolymerization product from the non-PHA waste that is insoluble in alcohol and water. About 1 to 10 mole percent water, preferably 1 to 3 mole percent, relative to the amount of alcohol can be used. The presence of the small amount of water at the depolymerizing/solubilizing temperature produces a liquid phase that can readily be separated from the insolubles at room temperature by filtration or the like.

The partial depolymerization product is low molecular weight polymer or an oligomer, the average molecular weight depending on the depolymerizations conditions of time, temperature and pressure of heating. Preferably, depolymerization with water present is continued long enough to yield a PHA depolymerization product with a molecular weight less than 50,000.

This process is used for the solubilizing by depolymerization of high molecular weight PHAs, and co- and ter-polymers therewith. It is most useful in the solubilizing of polylactide, polyglycolide and copolymers thereof; also it is useful for PHAs containing these polymer moieties polymerized with other monomers. These co- and ter-polymers preferably contain at least 70% of PLA and PGA moities, and not more than 30% of the other monomer. Examples of other suitable monomer units are:

epsilon-caprolactone,
delta-valerolactone,
1,5-dioxepan-2-one,
1,4-dioxan-2-one,
beta-butyrolactone,
beta-propiolactone, and
6-methyl-2,5-morpholinedione.

Other monomer units present in minor percents in the PHA to be recovered are not critical, the present process having wide applicability in depolymerizing, solubilizing, and recovering the monomer value of PHAs.

The amount of alcohol used affects the time required to carry out the necessary solubilization, and optimally also depolymerization when water is added. Normally a molar ratio of alcohol to PHA (on a PHA acid equivalent basis) in the range of 1:1 to 5:1, preferably 1.5:1 to 2.5:1, is used. Since an excess of alcohol favors solubilization, preferably a substantial excess is used, but not so much as to make product recovery an excessive expense.

The alcohols useful in the present invention are alkyl alcohols of one to six carbon atoms. n-butanol is by far the preferred alcohol because the butanol PHA solution can be used directly in an excellent process for the preparation of PHA described in Cockrem, U.S. Pat. No. 5,210,296.

An important aspect of the present invention is to use temperatures, and so pressures, adequate to cause the rapid dissolving and optionally depolymerization of the PHAs, but not severe enough to form undesirable degradation products.

Temperatures normally in the range of 100° to 250° C. or higher, preferably 100° to 200° C. are employed. In many cases, overall economics and reaction kinetics dictate running the process at atmospheric pressure although elevated pressure sometimes is needed to reach the necessary temperatures for rapid and complete solubilization. However, it may be desirable to use elevated pressures, up to about 1000 psi when high rates are desired.

Normally autogenous pressure is adequate. This is particularly true when the preferred n-butanol is used because its boiling point is well over 118° C. However, with lower alcohols, increased pressures may be needed to get the temperature into the 100° to 250° C. range necessary for liquefying the PHA.

By selecting optimal reaction conditions, particularly pressure and temperature, significant quantities of PHA can be adequately solubilized by a batch process often in 1 hour and even in as little as 15 minutes. Reactor design, i.e., agitation, etc., also plays an important role in reaction rate. Where speed is less a factor than other economies, batch times as long as 16 hours may be appropriate.

Continuous process depolymerization and dissolution is also possible, such as with the feed materials being continuously introduced into the first depolymerization stage of a multistage system, and the low molecular weight alcohol solution product being recovered from the last stage.

The following examples illustrate the preferred practice of the present invention.

EXAMPLE 1

A mixture of 100 grams polylactide (300,000 MW), 200 grams n-butanol, 0.5 grams brown bag, 2.0 grams bread, 5.0 grams sausage and 0.3 grams wax paper is heated to 118° C. for two hours in a 500 cc round bottom flask fitted with a reflux condenser. The resulting mixture is filtered thru a steam heated buchner funnel to separate the insoluble material. The solids are washed with 50 grams hot n-butanol. The polylactide separated as a solid on cooling to room temperature and was isolated by filtration.

EXAMPLE 2

A mixture of 75 grams polylactide, 150 grams n-butanol and 0.5 grams water is heated to 170° C. for one hour in a pressure vessel under autogenous pressure. The product is a liquid at room temperature and is easily pumped and transported for recovery and conversion to reusable polymer.

EXAMPLE 3

A mixture of 75 grams polylactide, 225 grams n-butanol and 2.0 grams water is heated to 170° C. for two hours in a pressure vessel under autogenous pressure. The product is a liquid at room temperature and is easily pumped and transported for recovery and conversion to useable polymer.

EXAMPLE 4

A mixture of 75 grams polylactide, 150 grams n-butanol is heated to 115° C. for ½ hour. The hot mixture is a liquid. The polylactide separated as a solid on cooling to room temperature and was separated by filtration.

EXAMPLE 5

A mixture of 100 grams polylactide (300,000 MW, 200 grams butanol, 5 grams water, 1.0 gram brown paper bag, 3.0 grams bread, 5.0 grams sausage and 0.5 grams wax paper is heated to 120° C. for two hours in a pressure vessel under autogenous pressure. The insolubles are separated by filtration. The filtrate contains partially depolymerized polylactide and oligomers.

EXAMPLE 6

Example 3 is repeated substituting 160 grams n-hexanol for the n-butanol. Solid polylactide was separated on cooling to room temperature.

EXAMPLES 7-10

The process of Example 4 is repeated using the following ingredients with similar results.

| Alcohol | Polymer |
| --- | --- |
| n-propanol | Copolymer of 80% lactic |

| Alcohol | Polymer | |
|---|---|---|
| | acid and 20% glycolic acid | |
| methanol | Compolymer of 90% lactic acid and 10% glycolic acid | |
| isopropanol | Copolymer of 80% lactic acid and 20% epsilon-caprolactone | |
| n-butanol | Copolymer of 90% lactic acid and 10% beta-propiolactone | |

What is claimed:

1. The process of recovering polyhydroxy acid polymer comprising:
   (a) mixing the polyhydroxy acid polymer with $C_1$–$C_6$ alkyl alcohol, said alcohol being present in an amount of at least 1 mole of alcohol per mole of hydroxy acid equivalent in said polymer; and
   (b) heating the resulting mixture to solubilize the polyhydroxy acid polymer, said heating being carried out at a temperature insufficient to significantly degrade said polymer.

2. The process of claim 1 wherein the mixture is heated to 100° to 200° C.

3. The process of claim 1 wherein the mixture is heated under autogenous pressure.

4. The process of claim 1 wherein the polymer contains at least a major proportion of polylactide.

5. The process of claim 1 wherein the polymer is polylactide.

6. The process of claim 1 wherein said polymer is selected from the group consisting of polylactide, polyglycolide, and polymers containing a major proportion of polylactide and polyglycolide copolymerized with up to 30% of another monomer selected from the group consisting of epsilon-caprolactone, delta-valerolactone, 1,5 dioxepen-2-one, 1,4 dioxan-2-one, beta-butyrolactone, beta-propiolactone, 6-methyl-2,5-morpholinedione and mixtures thereof.

7. The process of claim 2 wherein the time of heating is in the range of ¼–16 hours.

8. The process of claim 1, additionally comprising, following step (b):
   (c) cooling the resulting alcohol/polyhydroxy acid solution; and
   (d) recovering said polymer from said alcohol/polyhydroxy acid solution.

9. A process for recovering polyhydroxy acid value from a polyhydroxy acid polymer-containing source comprising the steps of:
   (a) contacting a polyhydroxy acid polymer-containing material, wherein said polyhydroxy acid polymer-containing material is contaminated with or constitutes trash, with at least one mole of a $C_1$ to $C_6$ alkyl alcohol per mole of hydroxy acid equivalent of said polyhydroxy acid polymer while maintaining the resulting mixture at sufficient temperature and pressure for a sufficient time to solubilize said polymer and form a liquid phase of enhanced polyhydroxy acid value, said temperature and pressure being insufficient to form undesirable degradation products; and
   (b) thereafter isolating and recovering said liquid phase.

10. The process of recovering polyhydroxy acid value from a polyhydroxy acid polymer, said process comprising:
    heating a mixture comprising the polyhydroxy acid polymer and a $C_1$–$C_6$ alkyl alcohol to form a liquid phase,
    said alcohol being present in an amount of at least 1 mole of alcohol per mole of hydroxy acid equivalent in said polymer, said alcohol comprising 1 to 10 mole percent water relative to the amount alcohol,
    said heating being carried out at a temperature at which partial depolymerization of the polyhydroxyl acid occurs.

11. The process of claim 10 wherein said heating is continued long enough to yield a depolymerization product with a molecular weight less than 50,000.

12. The process of claim 10 additionally comprising the step of separating said liquid phase from insolubles.

13. The process of claim 10 wherein the mixture is heated to 100° to 200° C.

14. The process of claim 10 wherein the mixture is heated under autogenous pressure.

15. The process of claim 10 wherein the polymer contains at least a major proportion of polylactic acid.

16. The process of claim 10 wherein the polymer is polylactic acid.

17. The process of claim 10 wherein said polymer is selected from the group consisting of polylactide, polymide, and polymers containing a major proportion of polylactide and polyglycolide polymerized with up to 30% of another monomer selected from the group consisting of epsilon-caprolactone, delta-valerolactone, 1,5-dioxepen-2-one, 1,4-dioxan-2-one, beta-butyrolactone, beta-propiolactone, 6-methyl-2, 5-morpholinedione and mixtures thereof.

18. The process of claim 13 wherein the time of heating is in the range of ¼–16 hours.

19. The process of claim 18 wherein the alcohol is n-butanol.

* * * * *